(12) United States Patent
Smith et al.

(10) Patent No.: US 8,556,804 B2
(45) Date of Patent: Oct. 15, 2013

(54) TORQUE-TRANSMITTING, VARIABLY FLEXIBLE INSERTION DEVICE AND METHOD FOR TRANSMITTING TORQUE AND VARIABLY FLEXING AN INSERTION DEVICE

(75) Inventors: Kevin Smith, Coral Gables, FL (US); Derek Deville, Miami, FL (US); Korey Kline, Miami, FL (US); Matthew Palmer, Miami, FL (US)

(73) Assignee: Syntheon, LLC, Miami, FL (US)

( * ) Notice: Subject to any disclaimer, the term of this patent is extended or adjusted under 35 U.S.C. 154(b) by 1124 days.

(21) Appl. No.: 11/804,843

(22) Filed: May 21, 2007

(65) Prior Publication Data

US 2007/0270648 A1 Nov. 22, 2007

Related U.S. Application Data

(60) Provisional application No. 60/802,466, filed on May 22, 2006.

(51) Int. Cl.
*A61B 1/00* (2006.01)

(52) U.S. Cl.
USPC .......................................... 600/139; 600/184

(58) Field of Classification Search
USPC .......... 606/139; 600/139, 104, 114, 140, 141, 600/142, 144, 146, 149, 184
See application file for complete search history.

(56) References Cited

U.S. PATENT DOCUMENTS

| | | | |
|---|---|---|---|
| 3,557,780 A | 1/1971 | Sato | |
| 3,998,216 A * | 12/1976 | Hosono | ..................... 600/140 |
| 4,176,662 A | 12/1979 | Frazer | |
| 4,575,185 A | 3/1986 | Wentzell et al. | |
| 4,753,223 A | 6/1988 | Bremer | |
| 4,815,450 A | 3/1989 | Patel | |
| 4,817,613 A | 4/1989 | Jaraczewski | |
| 4,838,859 A * | 6/1989 | Strassmann | ................ 604/95.03 |
| 4,890,602 A | 1/1990 | Hake | |
| 4,893,613 A | 1/1990 | Hake | |
| 4,998,282 A | 3/1991 | Shishido | |

(Continued)

FOREIGN PATENT DOCUMENTS

WO 2005048814 A2 6/2005

OTHER PUBLICATIONS

International Search Report for PCT/US07/05478 dated Dec. 17, 2007.

(Continued)

*Primary Examiner* — Kathleen Holwerda
*Assistant Examiner* — Sarah Simpson
(74) *Attorney, Agent, or Firm* — Mayback & Hoffman, P.A.; Gregory L. Mayback; Rebecca A. Tie

(57) ABSTRACT

A torque-transmitting, variably-flexible insertion device includes a hollow body having a proximal end with an entrance for receiving an instrument and a distal end with a tip for protrusion of the instrument. A vacuum-activated device transitions the hollow body between a relatively flexible condition and a relatively stiff condition. A torque braid transmits torque from the proximal end toward the distal end. A method for transmitting torque and variably flexing the insertion device includes transmitting torque along the hollow body with the torque braid, applying suction to create a vacuum in the hollow body for placing the hollow body in the relatively stiff condition, and relieving the vacuum for placing the hollow body in the relatively flexible condition.

44 Claims, 15 Drawing Sheets

(56) References Cited

U.S. PATENT DOCUMENTS

| | | | |
|---|---|---|---|
| D337,733 S | 7/1993 | Ewing et al. | |
| 5,259,366 A | 11/1993 | Reydel | |
| 5,337,733 A | 8/1994 | Bauerfeind | |
| 5,386,817 A | 2/1995 | Jones | |
| 5,577,992 A | 11/1996 | Chiba et al. | |
| 5,759,151 A | 6/1998 | Sturges | |
| 5,807,237 A | 9/1998 | Tindel | |
| 5,873,816 A | 2/1999 | Kagawa et al. | |
| 6,346,077 B1 * | 2/2002 | Taylor et al. | 600/204 |
| 6,375,654 B1 | 4/2002 | McIntyre | |
| 6,468,203 B2 | 10/2002 | Belson | |
| 6,506,150 B1 | 1/2003 | Ouchi | |
| 6,517,477 B1 | 2/2003 | Wendlandt | |
| 6,610,007 B2 | 8/2003 | Belson et al. | |
| 6,645,223 B2 | 11/2003 | Boyle et al. | |
| 6,800,056 B2 | 10/2004 | Tartaglia et al. | |
| 6,802,809 B2 | 10/2004 | Tartaglia et al. | |
| 6,858,005 B2 | 2/2005 | Ohline et al. | |
| 6,942,613 B2 | 9/2005 | Ewers et al. | |
| 6,984,203 B2 | 1/2006 | Tartaglia et al. | |
| 7,066,880 B2 * | 6/2006 | Wendlandt | 600/114 |
| 7,104,951 B2 | 9/2006 | Hasegawa et al. | |
| 2003/0135198 A1 | 7/2003 | Berhow et al. | |
| 2004/0044350 A1 * | 3/2004 | Martin et al. | 606/139 |
| 2004/0182393 A1 * | 9/2004 | MacMillan et al. | 128/205.19 |
| 2004/0186350 A1 | 9/2004 | Brenneman et al. | |
| 2005/0075538 A1 | 4/2005 | Banik et al. | |
| 2005/0131279 A1 * | 6/2005 | Boulais et al. | 600/141 |
| 2006/0069346 A1 | 3/2006 | Smith et al. | |
| 2007/0088367 A1 * | 4/2007 | Von Weymarn-Scharli | 606/108 |
| 2007/0179339 A1 | 8/2007 | Gorini et al. | |
| 2007/0208300 A1 | 9/2007 | Pravong et al. | |
| 2007/0272648 A1 | 11/2007 | Hamamoto et al. | |
| 2009/0149710 A1 | 6/2009 | Stefanchik | |

OTHER PUBLICATIONS

International Search Report for PCT/US07/012179 dated Sep. 12, 2008.
International Search Report for PCT/US07/075701 dated Aug. 29, 2008.
International Search Report for PCT/US08/064084 dated Dec. 9, 2008.
International Search Report for PCT/US08/068348 dated Oct. 30, 2008.
Abstract submitted to A/S/G/E, C W Williams, "A Split Overtube for Easier Colonoscopy", Gastrointestial Endoscopt, 1983, p. 188.

* cited by examiner

TORQUE-TRANSMITTING, VARIABLY FLEXIBLE INSERTION DEVICE AND METHOD FOR TRANSMITTING TORQUE AND VARIABLY FLEXING AN INSERTION DEVICE

CROSS-REFERENCE TO RELATED APPLICATIONS

This application claims the priority, under 35 U.S.C. §119 (e), of provisional application No. 60/802,466, filed May 22, 2006; the prior application is herewith incorporated by reference in its entirety.

BACKGROUND OF THE INVENTION

1. Field of the Invention

The invention relates to a torque-transmitting, variably-flexible insertion device. The invention also relates to a method for transmitting torque and variably flexing an insertion device.

2. Description of the Related Art

Insertion devices for surgical instruments are known in the art. Such devices include those which can transition between a relatively stiff and a relatively flexible condition, such as that disclosed in co-pending U.S. patent application Ser. No. 11/367,607, filed Mar. 2, 2006 and naming the inventors of the instant application.

A disadvantage of such variably flexing insertion devices is that the device twists when applying torque to the proximal end and therefore the torque is not transmitted along the device toward the distal end. This makes it difficult or impossible to impart a circumferential movement along the device when needed to traverse the body.

SUMMARY OF THE INVENTION

It is accordingly an object of the invention to provide a torque-transmitting, variably-flexible insertion device and a method for transmitting torque and variably flexing an insertion device, which overcome the hereinafore-mentioned disadvantages of the heretofore-known devices and methods of this general type and which transmit torque from the proximal end toward the distal end of the device. It is a further object of the invention to provide a simple yet effective measure for steering the insertion device.

With the foregoing and other objects in view there is provided, in accordance with the invention, a torque-transmitting, variably-flexible insertion device, comprising a hollow body having a proximal end with an entrance for receiving an instrument and a distal end with a tip for protrusion of the instrument. A vacuum-activated device transitions the hollow body between a relatively flexible condition and a relatively stiff condition. A torque braid transmits torque from the proximal end toward the distal end.

With the objects of the invention in view, there is also provided a method for transmitting torque and variably flexing an insertion device for receiving an instrument. The method comprises providing a hollow body, transmitting torque along the hollow body with a torque braid, applying suction to create a vacuum in the hollow body for placing the hollow body in a relatively stiff condition, and relieving the vacuum for placing the hollow body in a relatively flexible condition.

Other features which are considered as characteristic for the invention are set forth in the appended claims.

Although the invention is illustrated and described herein as embodied in a torque-transmitting, variably-flexible insertion device and a method for transmitting torque and variably flexing an insertion device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
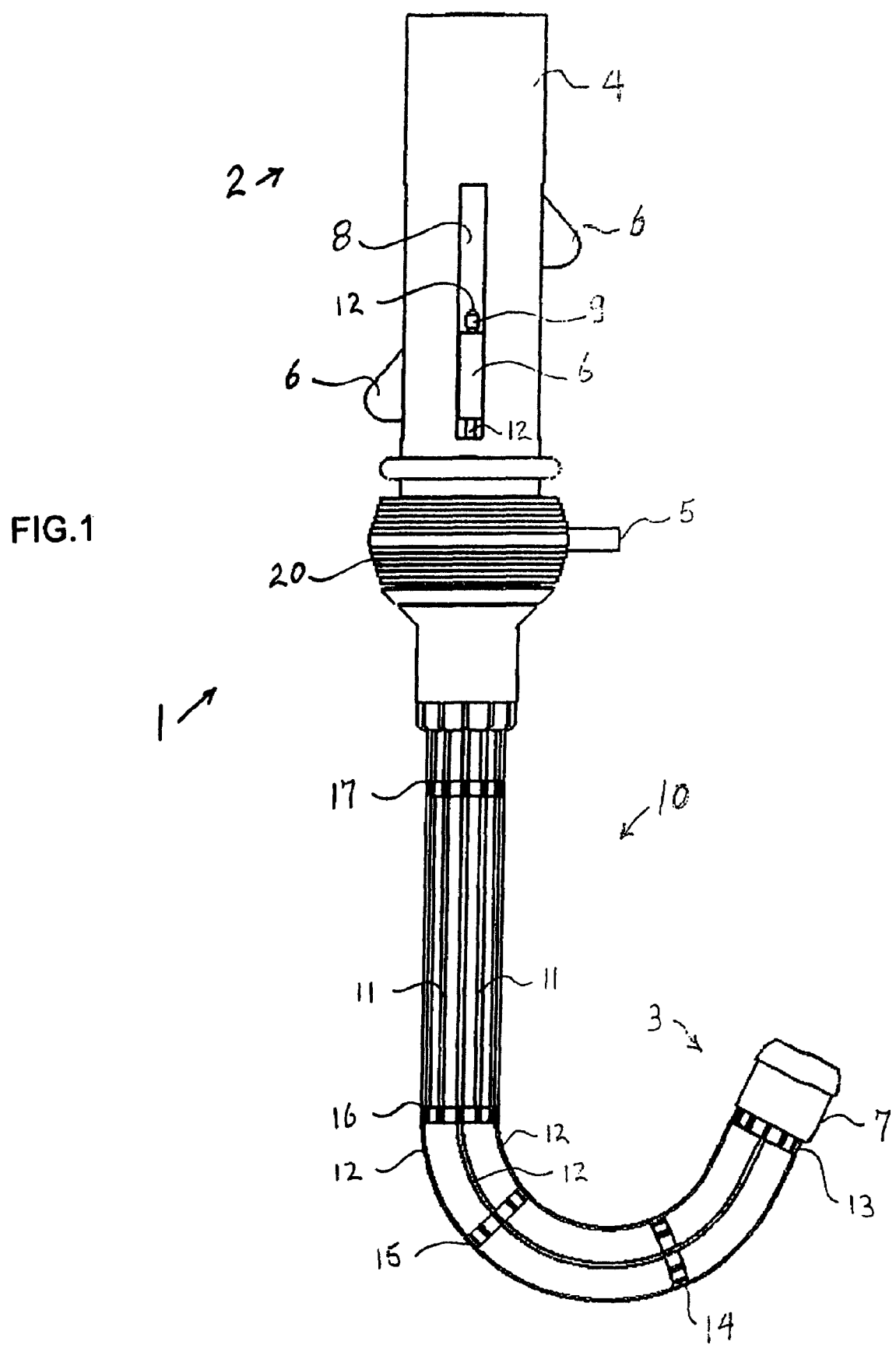
FIG. 1 is a diagrammatic, side-elevational view of a steerable, variably-flexible insertion device according to the invention, which has been steered to the right.
Figure 2:
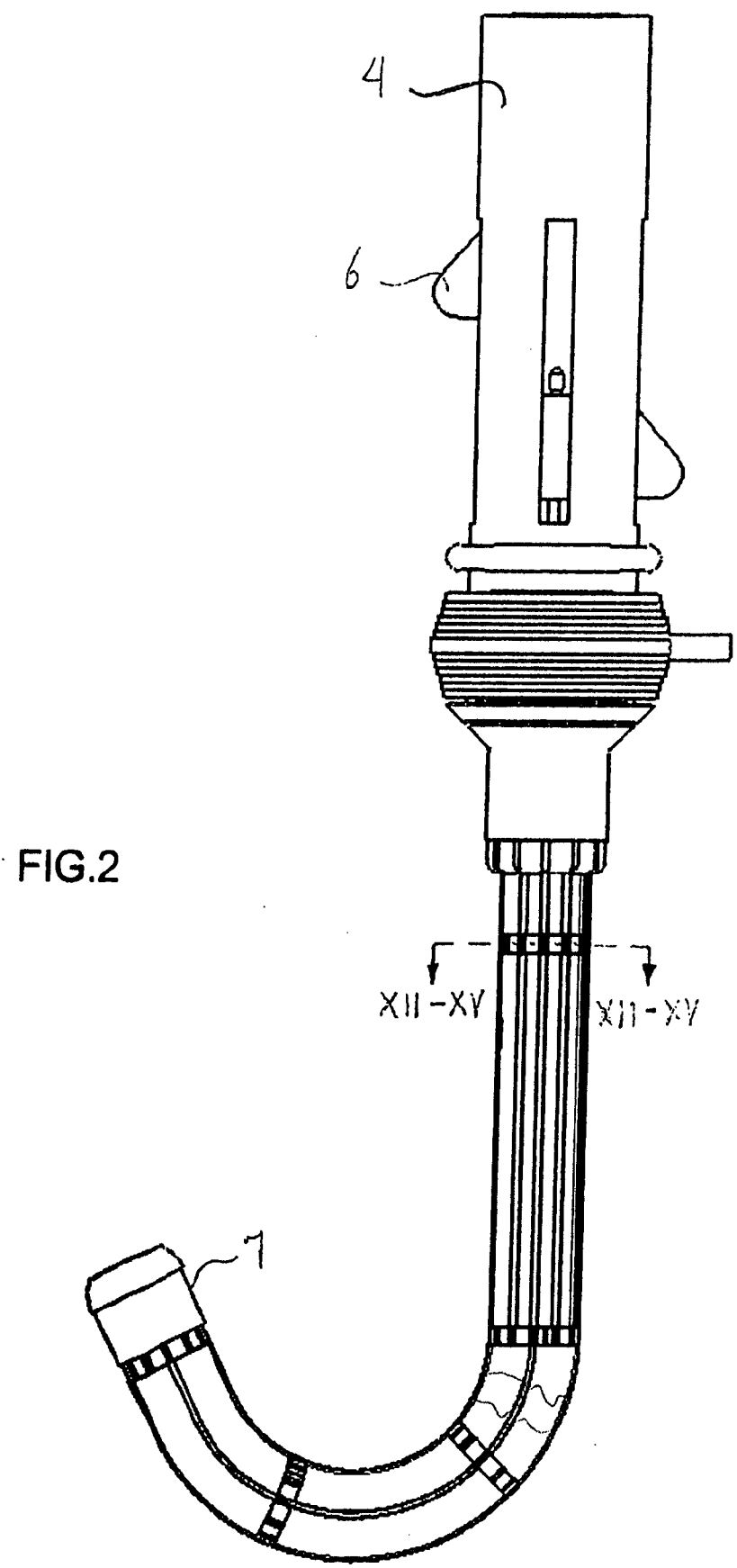
FIG. 2 is a view similar to FIG. 1, of the insertion device steered to the left.
Figure 3:
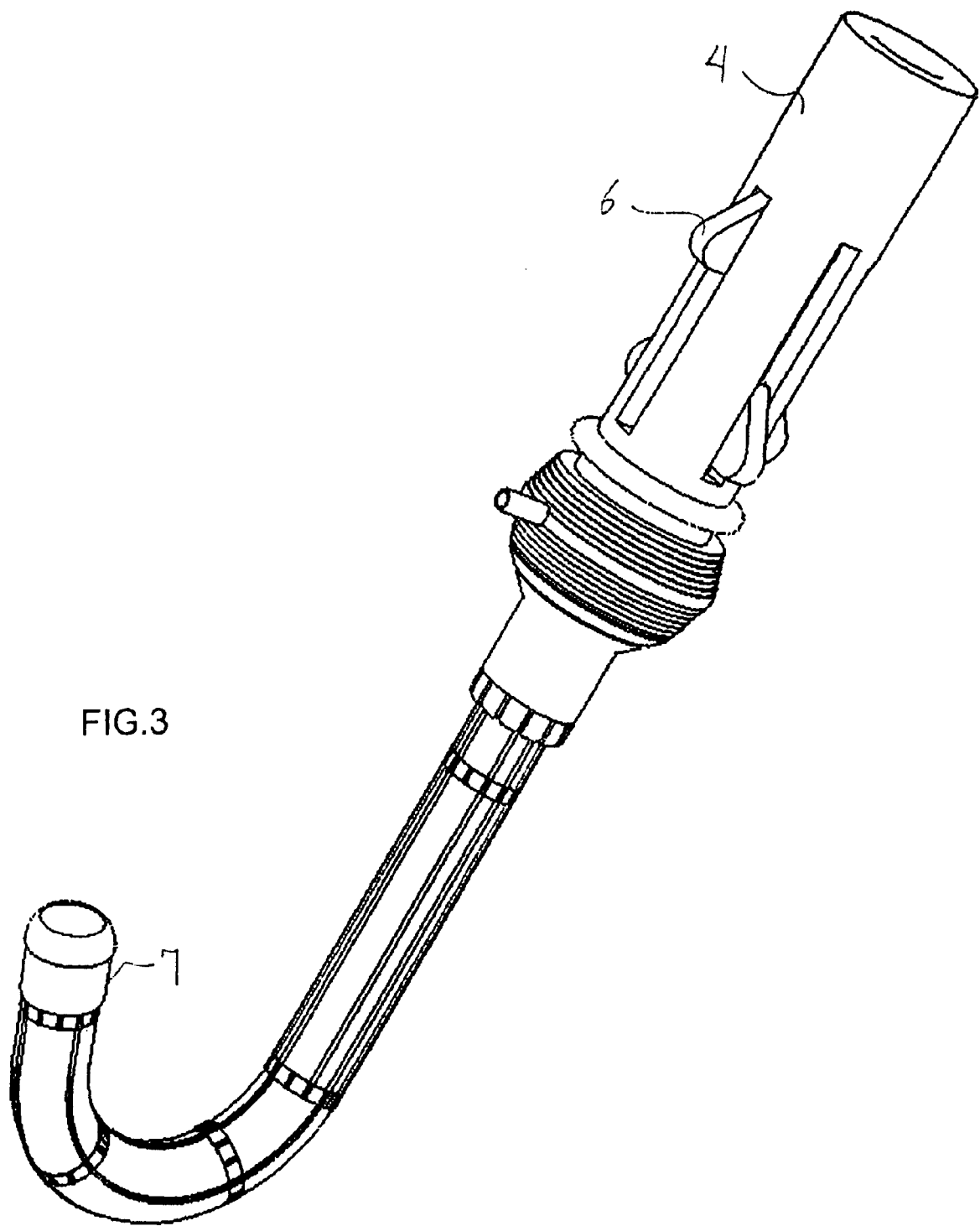
FIG. 3 is a perspective view of the insertion device of FIGS. 1 and 2.
Figure 10:
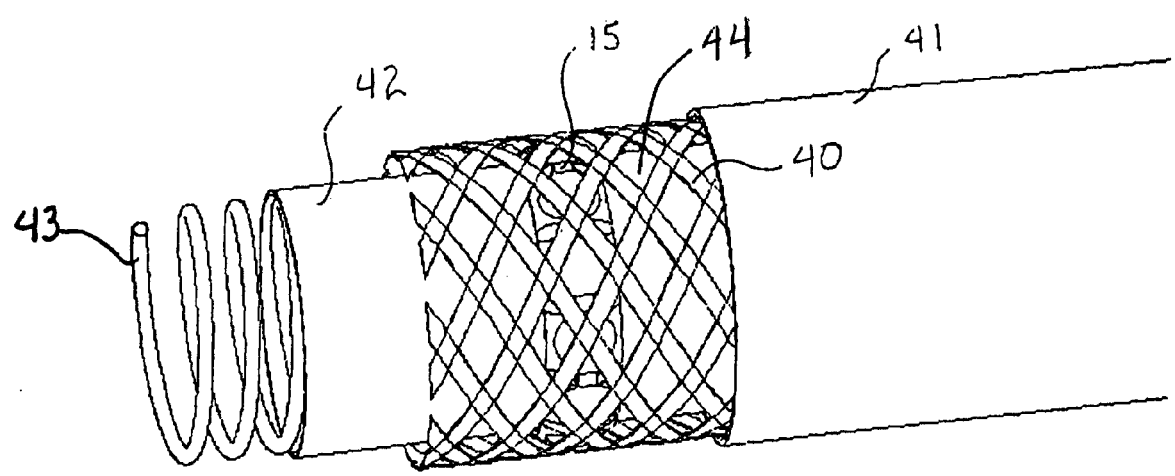
FIG. 10 is an enlarged, fragmentary, perspective view of the torque braid between an outer jacket and an inner sleeve covering a coil of the insertion device.

Referring now to the figures of the drawings in detail and first, particularly, to FIG. 1 thereof, there is seen a steerable, variably-flexible insertion device 1 according to the invention. The insertion device 1 has a hollow body with a proximal end 2 for manipulation by an operator and for receiving an instrument such as an endoscope or a colonoscope. The insertion device 1 also has a distal end 3 for insertion into a patient and for protrusion of the instrument. A handle 4 of the hollow body for control by the operator is disposed at the proximal end 2. The handle 4 has a vacuum connection or nipple 5 for controlling stiffness of the device, as will be explained below. An outer jacket 41 of the hollow body, which is disposed between the handle 4 and a tip 7 of the hollow body at the distal end 3, is not shown in FIG. 1. The outer jacket 41, which is shown in FIG. 10, provides a flexible section with a given length extending beyond the handle 4. Whereas FIG. 1 shows the hollow body steered to the right, FIG. 2 shows it steered to the left and FIG. 3 shows the hollow body in perspective.

A steering assembly 10 of the device 1 includes five vertebrae 13-17 shown as being disposed along the hollow body. However, more or fewer vertebrae can be provided in dependence on the length, diameter and use of the hollow body. Eight tendons are shown as being equally spaced apart about the circumference of the hollow body. A first four of those tendons, identified as non-steering tendons and indicated by reference numeral 11, extend only between the handle 4 and the vertebra 17 where they are fixed in place. A second four of those tendons, identified as steering tendons and indicated by reference numeral 12, are spaced apart by 90° circumferentially and extend between the handle 4 and the distal-most vertebra 13 where they are fixed in place. Once again, a greater or lesser number of tendons may be used, as needed. The tendons may have a rounded or flattened cross section or a flattened cross section twisted along its length. The vertebrae to which the tendons are fixed may be referred to as weld rings since the tendons may be welded thereto. For example, all of the tendons 12 are fixed to the vertebra 13, such as by welding. At the vertebra 16, for example, the steering tendons 12 are permitted to slide, but the non-steering tendons 11 are welded or otherwise fixed in place. When welding is used for fixation, the tendons and vertebrae are normally made of stainless steel. However, the tendons and vertebrae may also be formed of plastic which is bonded or adhesively connected where desired. Both metal and plastic tendons and vertebrae may be used in one device.

Figure 4:
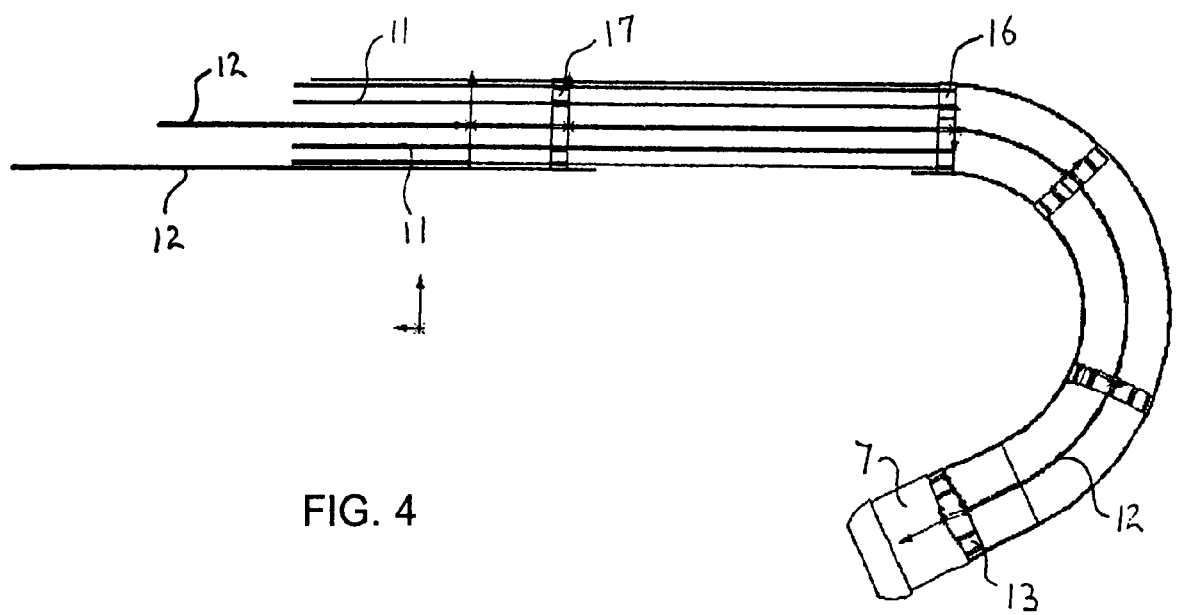
FIG. 4 is a fragmentary, side-elevational view of a steering assembly of the insertion device of the invention.

Four knobs 6 are each slideably disposed within a respective slot 8 in the handle 4. Each of the steering tendons 12 extend between the vertebra 13 and a respective one of the knobs 6. Each steering tendon 12 extends through a respective knob 6 and is connected to a respective stop 9. When a knob 6 is slid proximally, it pushes a stop 9 and pulls a steering tendon 12 to steer the hollow body. In the condition shown in FIG. 1, the knob 6 at the right has been slid proximally so that the tip 7 of the hollow body has been steered to the right. In the condition shown in FIG. 2, the knob 6 at the left has been slid proximally so that the tip 7 of the hollow body has been steered to the left. A similar result shown in FIG. 3 has been accomplished by sliding one of the knobs 6 proximally. When the knobs 6 are forced distally, the knobs can freely slide independently of the steering tendons 12 to prevent buckling of the steering tendons 12. It will be readily understood that if two of the knobs are slid proximally, the tip 7 will move in a direction between the two directions that each one of the knobs would have moved the tip if moved individually. FIG. 4 shows the device 1 with the handle 4 removed, from which it can be seen that the steering tendons 12 of the steering assembly 10 continue toward the handle from the tip 7, whereas the non-steering tendons 11 stop.

Figure 5:
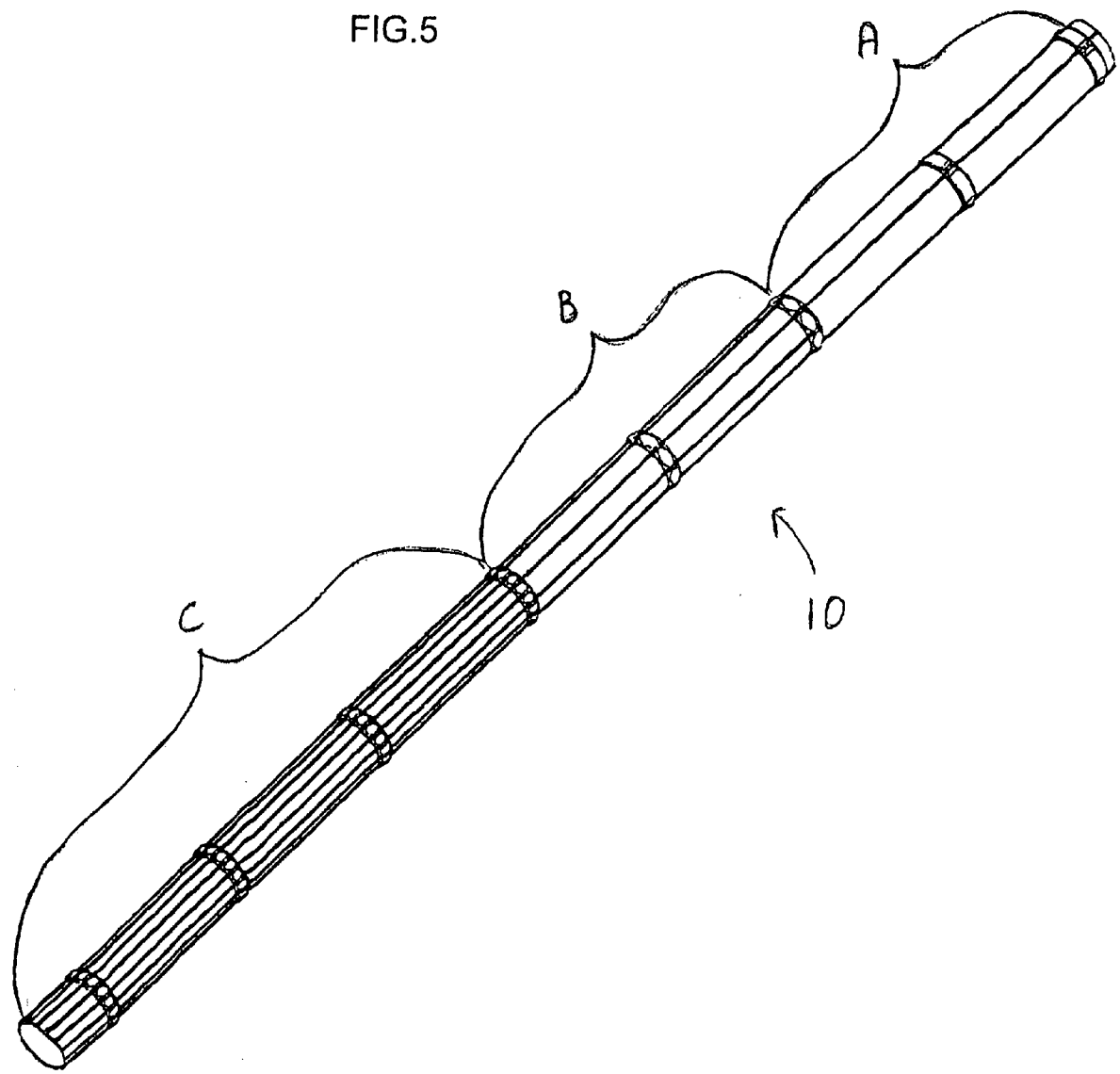
FIG. 5 is a perspective view of a stiffness zone assembly of the insertion device of the invention.

It is also possible, as shown in FIG. 5, to provide stiffness zones within the steering assembly 10. For example, a stiffness zone A closest to the distal tip 17 has four tendons, a stiffness zone B has eight tendons and a stiffness zone C closest to the handle 4 has sixteen tendons. A zone with more tendons will be stiffer than a zone with fewer tendons. The number of tendons and their location within the zones as well as the number of zones can be increased or decreased, depending on the application of the device. The vertebrae are also shown. The four tendons in the zone A are all fixed at the uppermost vertebra but are free to slide elsewhere. Four of the eight tendons in zone B, which do not extend to zone A, are fixed at the vertebra between zones A and B but are free to slide elsewhere. Similarly, eight of the sixteen tendons in zone C, which do not extend into zones A and B, are fixed at the vertebra between zones B and C but are free to slide elsewhere.

Figure 6:
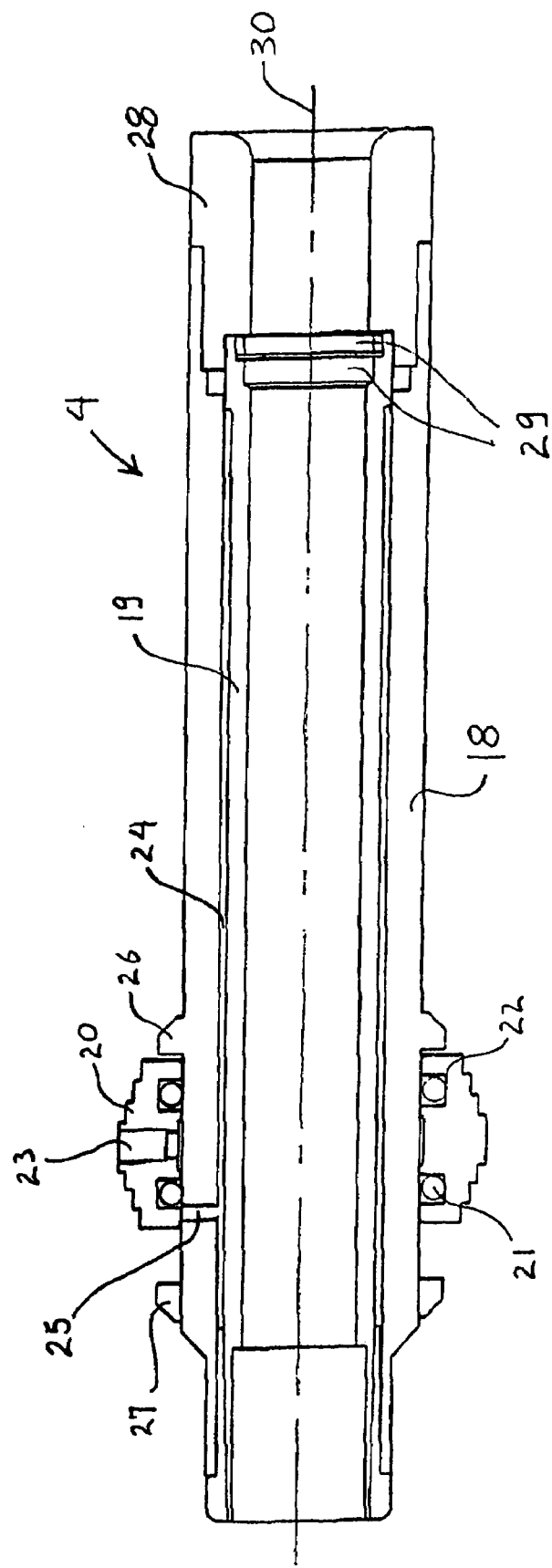
FIG. 6 is a longitudinal-sectional view of a sliding tire valve and side tube assembly of the insertion device of the invention.

FIG. 6 shows a cross-sectional view of the handle 4 of FIGS. 1-3, in which the connection or nipple 5, knobs 6 and slots 8 are not shown. The handle 4 has an inner handle 19 disposed within an outer handle 18, defining an annular vacuum plenum volume 24 therebetween which extends in longitudinal direction of the handle 4. A vacuum inlet/outlet hole or port 25 is formed in the body of the outer handle 18 and communicates with the volume 24. A sliding so-called tire valve thumb grip 20 encircles the outer handle 18 and is sealed thereto by O-ring seals having O-rings 21 in recesses 22 in the grip 20. The grip 20 also has a vacuum inlet/outlet 23 for the connection or nipple 5. When the grip 20 is slid toward an annular stop 26 as shown, the vacuum inlet/outlet 23 is not in alignment with the vacuum inlet/outlet hole 25. However, when the grip 20 is slid toward an annular stop 27, the vacuum inlet/outlet 23 and the vacuum inlet/outlet hole 25 are aligned, providing communication between the connection or nipple 5 and the volume 24. Therefore, during operation, the grip 20 is slid toward the stop 27 to apply vacuum to stiffen the hollow body or to vent the vacuum to the atmosphere or supply air at atmospheric pressure to make the hollow body flexible again. The grip 20 is slid toward the stop 26 to maintain the stiffened or flexible condition of the hollow body attained by vacuum or venting or air supply through the connection or nipple 5.

An end cap 28 is inserted into a proximal end of the outer handle 18 for insertion of an instrument, such as an endoscope or a colonoscope. End caps with various sized openings may be used in dependence on the instrument being used. The instrument passes through the hollow body and emerges at the distal tip 7. A diaphragm seal or so-called septum 29 is disposed between the end cap 28 and the inner handle 19. A dot-dash line 30 represents an instrument inserted through the handles.

Figure 7:
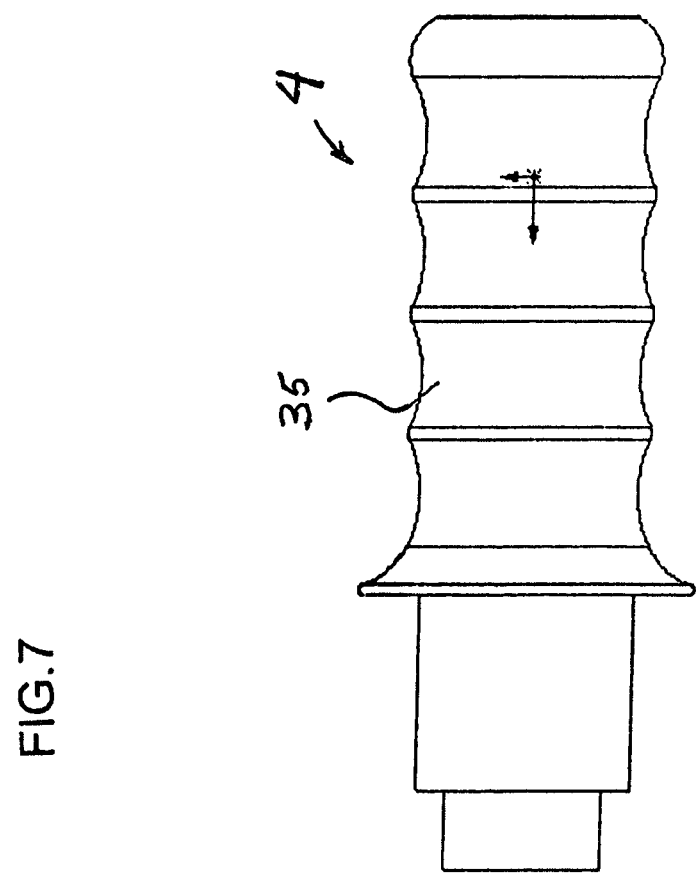
FIG. 7 is an elevational view of an ergonomically constructed valve handle to be used with the insertion device of the invention.
Figure 8:
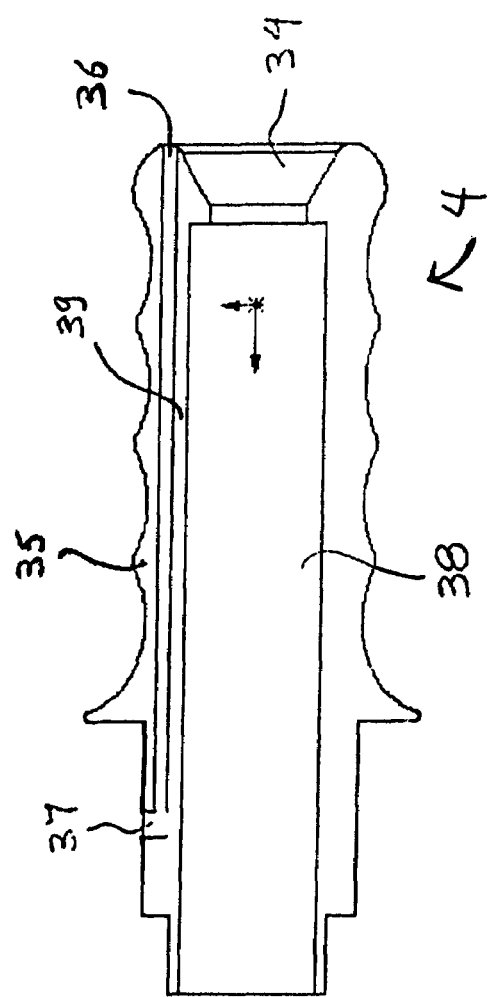
FIG. 8 is a longitudinal-sectional view of the handle of FIG. 7.

FIGS. 7 and 8 show a handle 4 with an outer vacuum valve handle 35 which is ergonomically configured with a so-called handlebar shape to be gripped by the hand of an operator of the device. A tire valve thumb grip 20 as is seen in FIG. 6 is also provided in the embodiment of FIGS. 6 and 7, but has been omitted for clarity. The outer handle 35 is an alternative to the outer handle 18. As can be seen from the cross section of FIG. 8, a vacuum source may be connected to a port 36 in the outer handle 35 and the vacuum inlet/outlet 23 of the tire valve thumb grip 20 may communicate with a vacuum inlet/outlet hole 37 leading to an annular vacuum plenum volume 39 between the outer handle 35 and an inner handle 38. When the tire valve thumb grip 20 is slid so that the vacuum inlets/outlets 23 and 37 are misaligned, vacuum is supplied from the port 36 to the vacuum plenum volume 39. When the tire valve thumb grip 20 is slid so that the vacuum inlets/outlets 23 and 37 are aligned, the plenum 39 is vented to the atmosphere. An end cap 34 is also shown.

Figure 9:
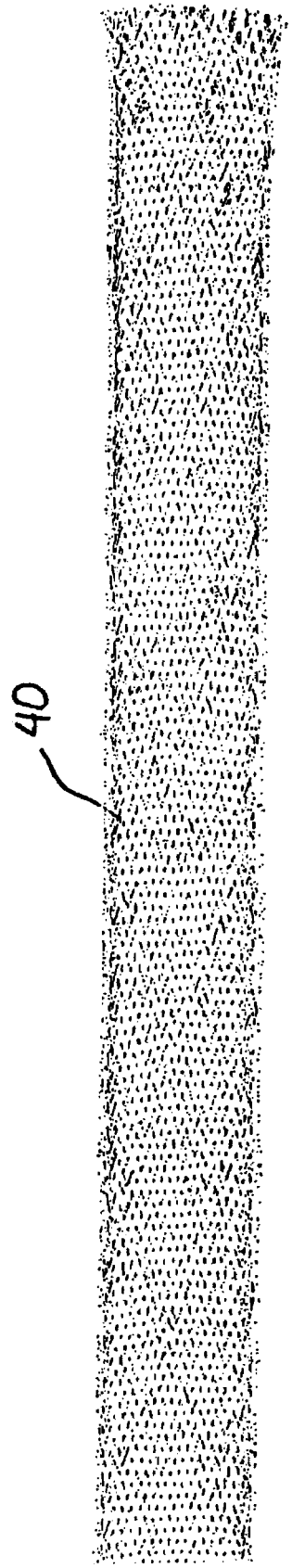
FIG. 9 is an elevational view of a torque braid of the insertion device of the invention.

FIG. 9 illustrates a torque sheath or braided inner liner 40 of the insertion device 1. The torque braid 40 is a woven tube formed of fabric, plastic, metal or a combination thereof, such as a metallized material. Steel or a polymer, such as polyethylene terephthalate or PET (sold under the trademark MYLAR) or PEEK (polyether ether ketone) are particularly useful. The purpose of the torque braid 40 is to transmit torque applied by the operator of the device at the proximal end 2 along the length of the hollow body up to the tip 7. Therefore, the torque braid must be non-linearly compliant, that is it has a limited elongation in the linear direction.

As is shown in the perspective view of FIG. 10, the torque braid 40 may be disposed in a space 44 between an outer jacket 41 and an inner sleeve 42. In the illustrated embodiment, the torque braid 40 is disposed above the vertebra 15, but the tendons have been omitted for clarity. The torque braid 40 may be placed in various locations, as will be described below with reference to FIGS. 12-15. The purpose of the torque braid 40 is to allow twisting of the hollow body as well as steering of the hollow body by the tendons while inserting the insertion device into the body. The torque braid 40 is typically provided over the full length of the hollow body, but may also be omitted at the tip 7 for additional flexibility or doubled, for instance, near the handle 4 for additional stiffness.

FIG. 10 also shows a coil 43 of the hollow body which is provided within the inner sleeve 42 of the hollow body for supporting the inner sleeve. The coil may be a wire which is TEFLON- or hydrophilic-coated to ease insertion of an endoscope or colonoscope. The stiffness or spring constant k of the coil 43 tends to maintain the device 1 in a straight condition and is used to maintain the round cross section of the device 1 while it is flexed.

Figure 11:
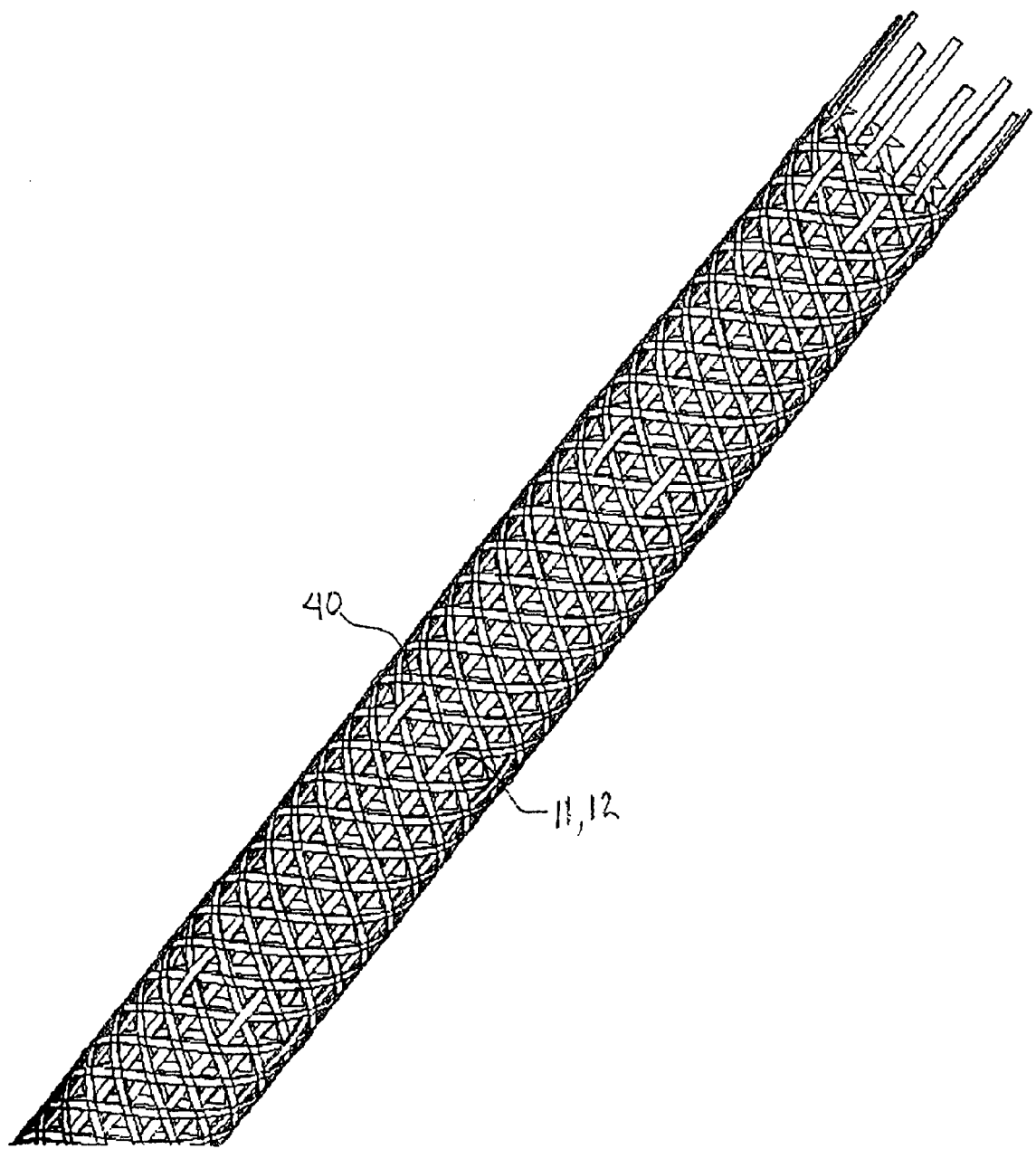
FIG. 11 is a fragmentary, perspective view showing tendons intermittently woven through the torque braid.

FIG. 11 shows an alternative embodiment of the torque braid 40 and the tendons 11, 12, in which the tendons are intermittently woven through the torque braid to eliminate the need for the vertebrae 13-17. The tendons 11, 12 travel under the torque braid 40 for about 2 inches and then are woven through one loop of the torque braid 40 to create weave points. This is repeated along the length of the device. The weave points act like the vertabrae in "attaching" the tendons 11, 12 to the body of the device but letting the tendons slide through. Using the torque braid in this way eliminates the need for the vertabrae thus decreasing the outer diameter of the device, lowering the cost of the device and simplifying the structure thereof. It is noted that the tendons are shown as being flexed as they weave through the torque braid for clarity of the illustration. In actuality there will be some amount of flex in both the torque braid and the tendons, but mostly on the part of the torque braid. The tendons could also be woven in the opposite way, that is laid on top of the braid and woven down into it.

FIGS. 12-15 are cross-sectional views of the device, in which the torque braid 40 is placed in various locations. In each of the figures, as seen from the exterior toward the interior, the insertion device 1 includes the outer jacket 41, the space 44, the vertebrae 13-17 (reference numeral 15 is used as an example), the inner sleeve 42 and the coil 43, although the latter is merely shown in outline form for the sake of clarity. It is also seen that the vertebrae 13-17 have channels 45 formed therein permitting movement of the tendons 11, 12 which are not fixed in place.

Figure 12:
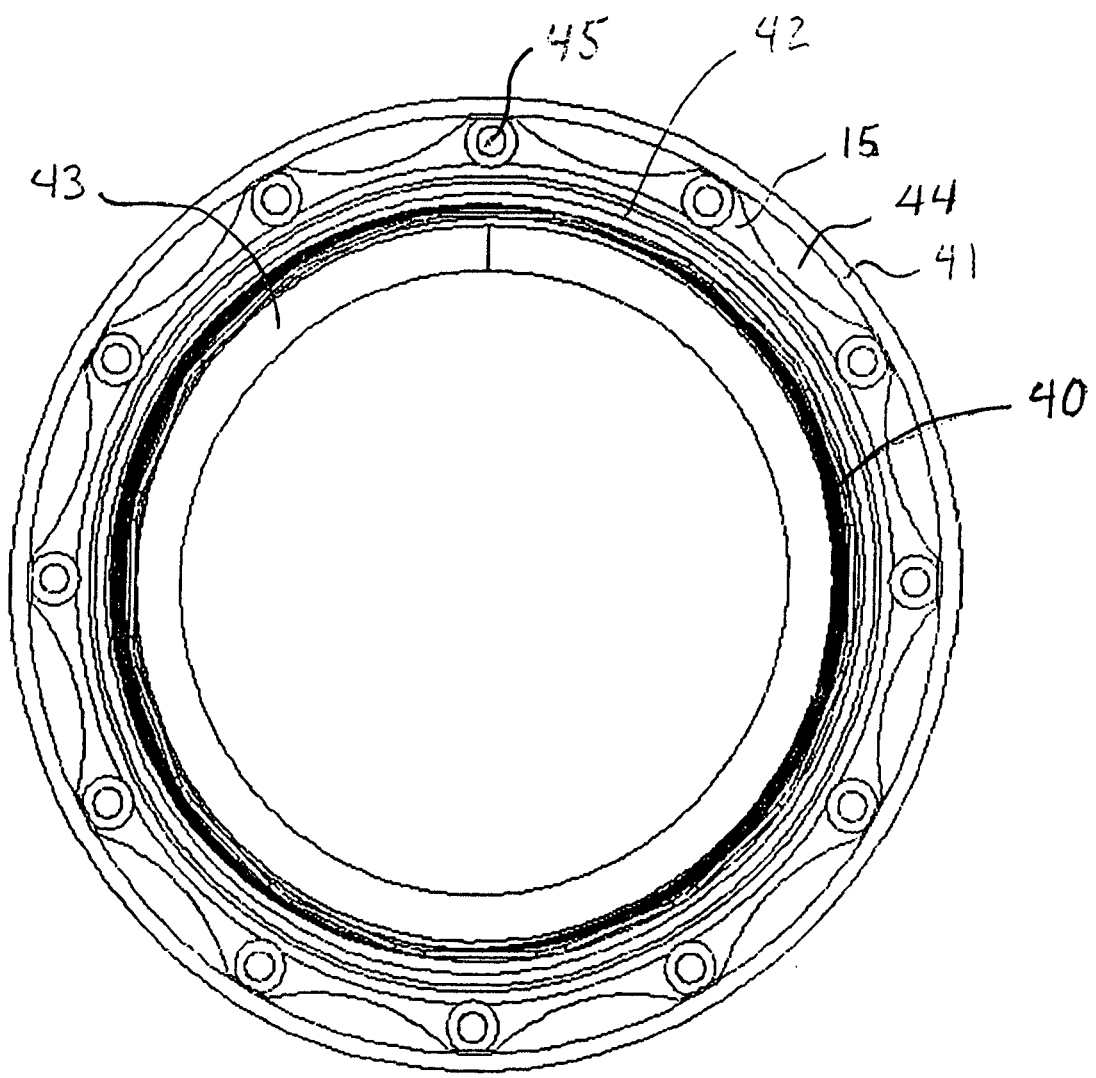
FIGS. 12, 13, 14 and 15 are cross-sectional views of the insertion device of the invention, which are taken along a line XII-XV of FIG. 2, in the direction of the arrows, but with the torque braid in various locations.
Figure 13:
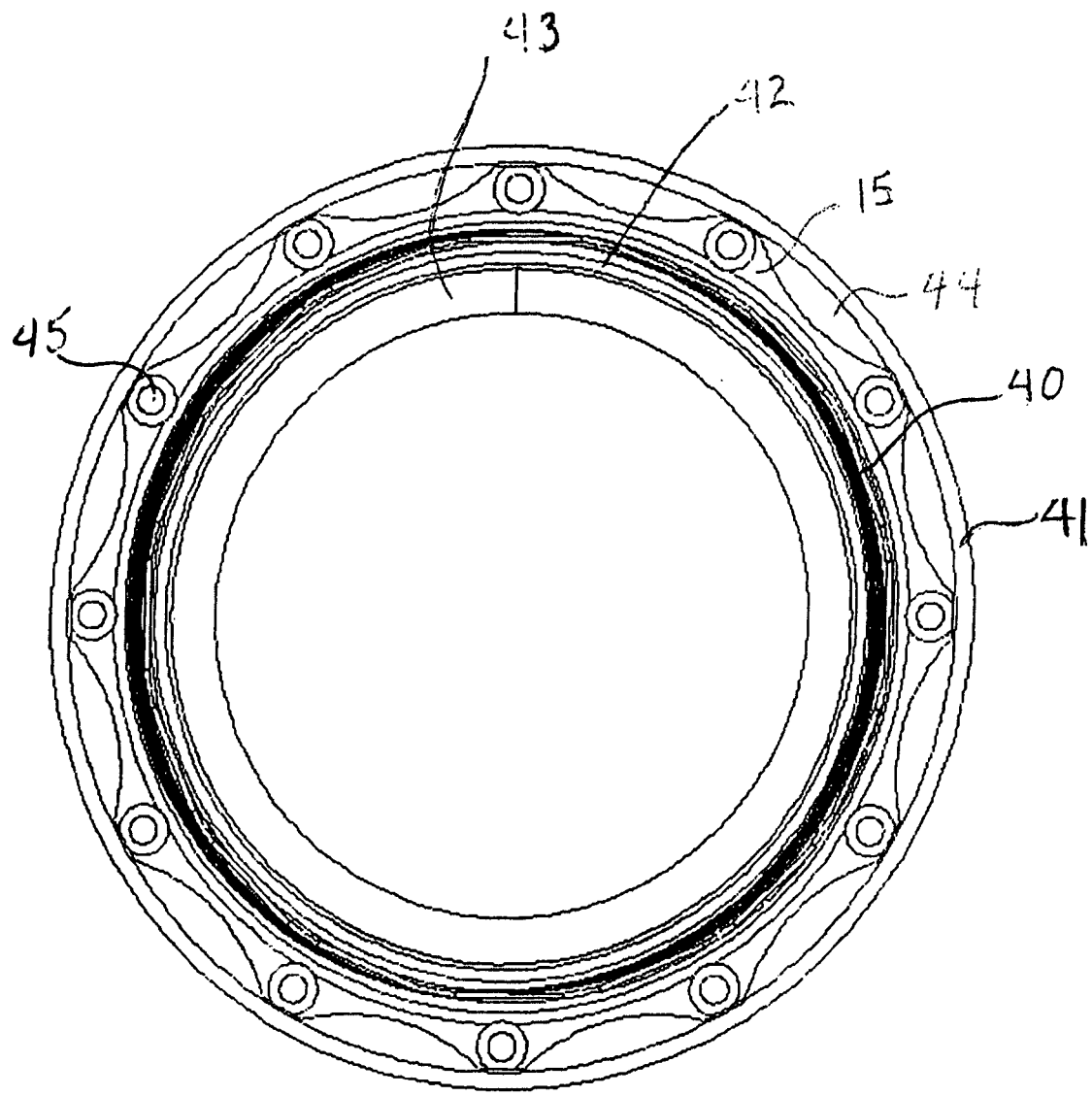
Figure 14:
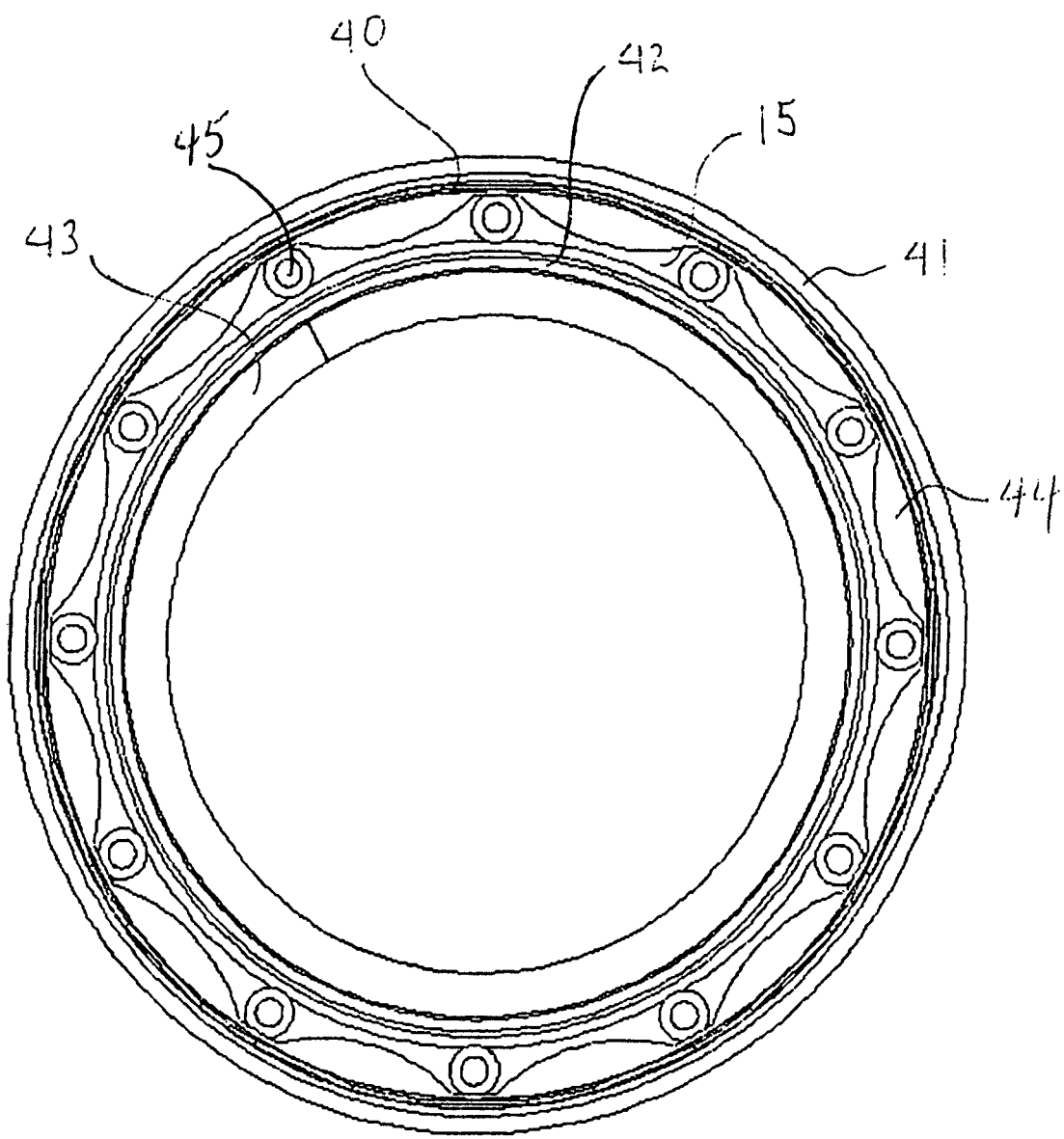
Figure 15:
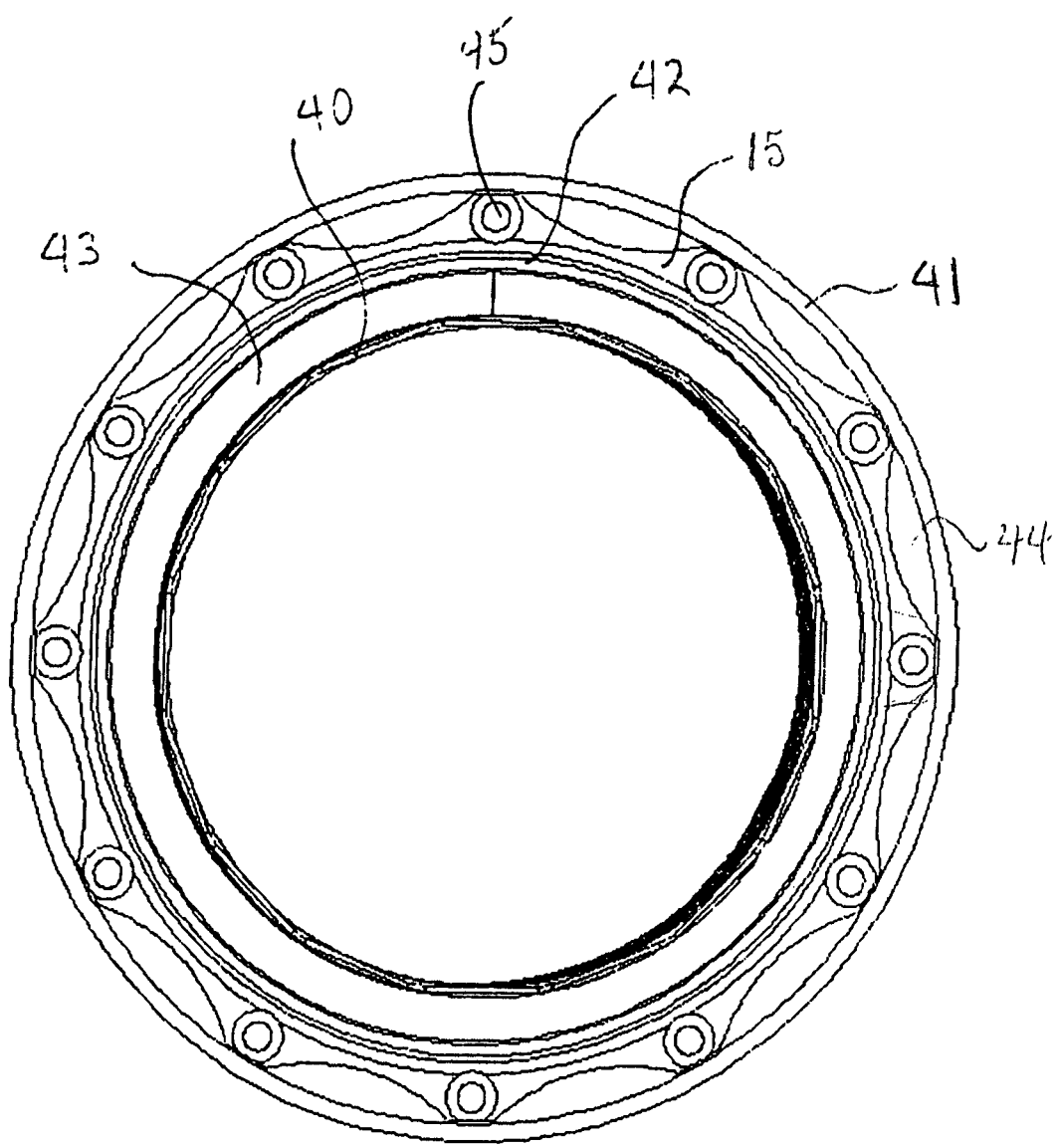

In the embodiment of FIG. 12, the torque braid 40 is disposed between the coil 43 and the inner sleeve 42. In the embodiment of FIG. 13, the torque braid 40 is disposed between the inner sleeve 42 and the vertebra 15. In the embodiment of FIG. 14, the torque braid 40 is disposed between the vertebra 15 and the outer jacket 41. In the embodiment of FIG. 15, the torque braid 40 is disposed within the coil 43.

The operation of the variably flexible insertion device 1 will now be described below by making reference to the above-described figures. The device 1 is flexed against the stiffness or spring constant k of the coil 43, for example upon traversing the rectosigmoid junction, by sliding one or more of the knobs 6. If it is desired to maintain that flexed condition for guiding an endoscope, such as a colonoscope, vacuum is applied at the connection or nipple 5 in the embodiment of FIG. 6 or at the vacuum port 36 in the embodiment of FIG. 8. When suction is applied to create the vacuum, it causes the inner sleeve 42 and the outer jacket 41 to firmly contact each other with the tendons 11, 12 sandwiched and frictionally locked therebetween. Therefore, the vacuum connection or nipple 5 or the vacuum port 36 acts as a device for transitioning the hollow body 4/35, 7, 19/38, 41, 42, 43 between a relatively flexible condition and a relatively stiff condition through the application of a vacuum. As long as the vacuum is applied, the device 1 maintains its flexed condition. The positions of the knobs 6 in FIGS. 1-3 show that in the flexed condition, the tendons 12 at the outer periphery of the bend become shorter and the tendons 12 at the inner periphery of the bend become longer, since they are all fixed in place at the first vertebra 13.

The tendons or wires are passive elements which are not in tension at any time. The tendons float within the hollow body when it is in the flexible condition, except where they are fixed to vertebra, such as at the distal end. The tendons are frictionally locked by the inner sleeve 42 and the outer jacket 41 when the hollow body is in the stiff condition. However, in both the relatively flexible condition and the relatively stiff condition, the tendons have no active control imposed on them and are not pulled or constrained.

When it is desired to resume flexibility of the device 1, the vacuum is vented or replaced by air at ambient or positive pressure. This causes the inner sleeve 42 and the outer jacket 41 to release the tendons and allows the stiffness or spring constant k of the coil 43 to place the device 1 into its normally flexible condition.

The device is intended to be used in a manner similar to prior art devices. Therefore, the device will be placed over the endoscope. The endoscope will then be inserted into the rectum. The device will then be pushed in its flexible condition, to follow the curvature of the scope. The device will then be stiffened, allowing the scope to be pushed forward with less pressure exerted on the colon of the patient. This procedure can be repeated until the scope reaches the cecum.

An alternative use of the device is to aid in small bowel endoscopy. The device is placed over the endoscope. The endoscope is inserted into the patient transorally, through the stomach and then partially into the small bowel. The device is then pushed in its flexible condition, to follow the curvature of the scope. The device is then stiffened, allowing the scope to be pushed forward without the scope looping in the stomach.

Another use of the device is for aiding in access to internal body parts, such as the gallbladder, through an opening of an internal body cavity, such as the stomach. The device is placed over the endoscope. The endoscope is inserted into the patient transorally, through the stomach and then up against the internal surface of the stomach. The device is then pushed in its flexible condition, to follow the curvature of the scope. The device is then stiffened, allowing the surgeon to create an opening in the stomach wall without the scope looping in the stomach. Once the opening is created, the device and the scope can be advanced outside the stomach. The device can then be stiffened to create a stable platform to perform surgical procedures outside of the stomach. The device could contain one or more features (i.e. balloons) for sealing the outer periphery of the device to the stomach wall to prevent gastric fluids from exiting the stomach.

In each of these procedures described above, the knobs and tendons are used to steer the insertion device within the body as needed, while the torque braid allows the device to be twisted as needed.

We claim:

1. A torque-transmitting, variably-flexible insertion device, comprising:
   a hollow body with a given length having a proximal end with an entrance for receiving an instrument and a distal end with a tip for protrusion of the instrument;
   a vacuum-activated device for transitioning said hollow body between a relatively flexible condition and a relatively stiff condition;
   a torque braid for transmitting torque from said proximal end toward said distal end; and
   tendons disposed within said hollow body, said vacuum-activated device operable to apply suction to said hollow body to thereby frictionally lock said tendons in place selectively to maintain said hollow body in said relatively flexible and relatively stiff conditions, wherein said tendons are not under tension in both said relatively flexible and relatively stiff conditions.

2. The insertion device according to claim 1, wherein said torque braid is disposed within said hollow body extending substantially entirely over said given length.

3. The insertion device according to claim 1, wherein at least some of said tendons are individually adjustable in length for steering said distal end of said hollow body.

4. The insertion device according to claim 1, which further comprises a coil disposed within said hollow body, said coil tending to maintain said hollow body with an approximately round cross section and in a straight condition when in said relatively flexible condition.

5. The insertion device according to claim 4, wherein said torque braid is disposed within said coil.

6. The insertion device according to claim 1, wherein said hollow body has an outer jacket and an inner sleeve defining a space therebetween, said tendons are at least partly disposed in said space, and said vacuum-activated device applies suction to said space for frictionally locking said tendons in place.

7. The insertion device according to claim 6, wherein said vacuum-activated device is a vacuum connection communicating with said space.

8. The insertion device according to claim 7, wherein said hollow body has a handle at said proximal end, said handle has an outer handle and an inner handle defining a vacuum plenum volume therebetween communicating with said space, and said handle has a vacuum port communicating with said vacuum plenum volume.

9. The insertion device according to claim 8, which further comprises a sliding valve encircling said outer handle and having a vacuum inlet/outlet formed therein for communicating with said vacuum connection, said sliding valve sliding between a position in which said vacuum inlet/outlet communicates with said vacuum port and a position in which said vacuum inlet/outlet is sealed against said vacuum port.

10. The insertion device according to claim 9, wherein said sliding valve has a recess formed therein receiving an O-ring for sealing said sliding valve to said outer handle.

11. The insertion device according to claim 6, which further comprises a coil disposed within said hollow body, said coil tending to maintain said hollow body with an approximately round cross section and in a straight condition when in said relatively flexible condition, said torque braid being disposed between said coil and said inner sleeve.

12. The insertion device according to claim 6, which further comprises vertebrae disposed within said hollow body for guiding said tendons, said torque braid being disposed between said inner sleeve and said vertebrae.

13. The insertion device according to claim 6, which further comprises vertebrae disposed within said hollow body for guiding said tendons, said torque braid being disposed between said vertebra and said outer jacket.

14. The insertion device according to claim 1, which further comprises vertebrae disposed within said hollow body for guiding said tendons.

15. The insertion device according to claim 14, wherein some of said vertebrae have channels formed therein permitting movement of some of said tendons.

16. The insertion device according to claim 14, wherein said vertebrae include a distal-most vertebra at which some of said tendons are attached.

17. The insertion device according to claim 16, wherein said tendons include steering tendons attached to said distal-most vertebra and non-steering tendons attached to another of said vertebrae other than said distal-most vertebra.

18. The insertion device according to claim 1, wherein said hollow body has a handle and a flexible section with a given length, and said tendons extend substantially entirely over said given length.

19. The insertion device according to claim 18, wherein said tendons float in said handle when said hollow body is in said relatively flexible condition.

20. The insertion device according to claim 1, wherein said hollow body has a handle, and said tendons are rigidly attached at said distal end and allowed to float at said handle.

21. The insertion device according to claim 1, which further comprises vertebrae disposed within said hollow body for guiding said tendons, said vertebrae being attached to some of said tendons.

22. The insertion device according to claim 1, wherein said tendons vary in number along said hollow body for providing zones of varying stiffness.

23. The insertion device according to claim 22, wherein said number of said tendons is greater toward said distal end than toward said proximal end for increasing stiffness at said distal end.

24. The device according to claim 1, wherein the instrument is a scope.

25. A method for transmitting torque and variably flexing an insertion device for receiving an instrument, the method comprising the following steps: providing a hollow body having a given length and a proximal end with an entrance for receiving an instrument and a distal end with a tip for protrusion of the instrument; providing tendons within said hollow body; transmitting torque along the hollow body from said proximal end toward said distal end with a torque braid; applying suction to create a vacuum in the hollow body to thereby frictionally lock said tendons in place selectively to maintain the hollow body in a relatively stiff condition; and relieving the vacuum to place the hollow body in a relatively flexible condition, wherein said tendons are not under tension in both said relatively stiff and relatively flexible conditions.

26. The method according to claim 25, which further comprises steering the hollow body by sliding the tendons.

27. The method according to claim 26, which further comprises varying a stiffness of the hollow body zonally by varying a number of the tendons along the hollow body.

28. The method according to claim 27, which further comprises increasing the stiffness of the hollow body by providing a greater number of the tendons in a zone of greater stiffness.

29. The method according to claim 25, which further comprises providing the hollow body with an inner sleeve and an outer jacket defining a space therebetween, and sandwiching the tendons in the space in the relatively stiff condition.

30. The method according to claim 25, which further comprises providing the hollow body with an inner sleeve and an outer jacket defining a space therebetween, and applying the vacuum in the space in the relatively stiff condition.

31. The method according to claim 30, which further comprises providing a coil in the hollow body tending to maintain the hollow body with an approximately round cross section and in a straight condition when in the relatively flexible condition, and sandwiching the torque braid between the coil and the inner sleeve.

32. The method according to claim 30, which further comprises guiding the tendons with vertebrae disposed within the hollow body, and sandwiching the torque braid between the inner sleeve and the vertebrae.

33. The method according to claim 30, which further comprises guiding the tendons with vertebrae disposed within the hollow body, and sandwiching the torque braid between the vertebra and said outer jacket.

34. The method according to claim 25, wherein the hollow body has a handle and the tendons float in the handle when the hollow body is in the relatively flexible condition.

35. The method according to claim 25, which further comprises maintaining a circular cross section of the hollow body with a coil.

36. The method according to claim 35, which further comprises placing the torque braid within the coil.

37. The method according to claim 25, wherein the tendons are not in compression when the hollow body is in the relatively stiff condition.

38. The method according to claim 25, wherein the instrument is a scope.

39. The method according to claim 25, which further comprises maintaining the tendons in a non-tensioned state in both the relatively stiff and the relatively flexible conditions of the hollow body.

40. The method according to claim 25, which further comprises guiding the tendons with vertebrae disposed within the hollow body.

41. The method according to claim 40, which further comprises guiding the tendons through channels formed in some of the vertebrae.

42. The method according to claim 25, which further comprises providing the hollow body with an inner sleeve and an outer jacket, and sandwiching the torque braid between the inner sleeve and the outer jacket in the relatively stiff condition.

43. The method according to claim 25, which further comprises providing a handle on the hollow body, and transitioning between the relatively stiff and relatively flexible conditions by sliding a sliding valve along the handle.

44. The method according to claim 25, which further comprises fixing some of the tendons in place and sliding others of the tendons for steering only a distal portion of the hollow body.

* * * * *